(12) United States Patent
Litterst et al.

(10) Patent No.: US 11,584,960 B2
(45) Date of Patent: Feb. 21, 2023

(54) MULTIPLEX DETECTION OF SHORT NUCLEIC ACIDS

(71) Applicant: Roche Molecular Systems, Inc., Pleasanton, CA (US)

(72) Inventors: Claudia Litterst, Walnut Creek, CA (US); Ha Bich Tran, Daly City, CA (US); Wei Yang, Dublin, CA (US)

(73) Assignee: Roche Molecular Systems, Inc., Plesanton, CA (US)

( * ) Notice: Subject to any disclaimer, the term of this patent is extended or adjusted under 35 U.S.C. 154(b) by 158 days.

(21) Appl. No.: 16/130,656

(22) Filed: Sep. 13, 2018

(65) Prior Publication Data

US 2019/0078136 A1    Mar. 14, 2019

Related U.S. Application Data

(60) Provisional application No. 62/558,209, filed on Sep. 13, 2017.

(51) Int. Cl.
| | |
|---|---|
| *C12Q 1/686* | (2018.01) |
| *C12Q 1/6853* | (2018.01) |
| *C12Q 1/6806* | (2018.01) |
| *C12N 15/10* | (2006.01) |
| *C12Q 1/6809* | (2018.01) |

(52) U.S. Cl.
CPC ............ *C12Q 1/686* (2013.01); *C12N 15/10* (2013.01); *C12Q 1/6806* (2013.01); *C12Q 1/6809* (2013.01); *C12Q 1/6853* (2013.01); *C12N 2310/3231* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 2007/0048757 A1 | 3/2007 | Lao et al. | |
| 2016/0186259 A1* | 6/2016 | Ofir | C12Q 1/6881 435/325 |
| 2017/0233801 A1* | 8/2017 | Kubista | C12Q 1/6853 435/6.11 |

FOREIGN PATENT DOCUMENTS

KR    20160127517 A    11/2016

OTHER PUBLICATIONS

Androvic et al.,"Two-tailed RT-qPCR: a novel method for highly accurate miRNA quantification", Nucleic Acids Research, vol. 45, No. 15, Jul. 13, 2017 (Jul. 13, 2017), pp. e144-e144, XP055517760, ISSN: 0305-1048, DOI: 10.1093/nar/gkx588 the whole document.
International Search Report and Written Opinion dated Oct. 31, 2018 in corresponding PCT/EP2018/074692 filed on Sep. 13, 2018, pp. 1-15.
Shozo Honda et al: "Dumbbel-PCR: a method to quantify specific small RNA variants with a single nucleotide resolution at terminal sequences", Nucleic Acids Research, vol. 43, No. 12, Mar. 16, 2015, pp. 1-12, XP055366207, ISSN: 0305-1048, DOI: 10.1093/nar/gkv218 the whole document.

* cited by examiner

*Primary Examiner* — Samuel C Woolwine
(74) *Attorney, Agent, or Firm* — David J. Chang

(57) ABSTRACT

Provided herein are methods and compositions for performing multiplex RT-PCR to amplify short nucleic acids.

16 Claims, 5 Drawing Sheets

Specification includes a Sequence Listing.

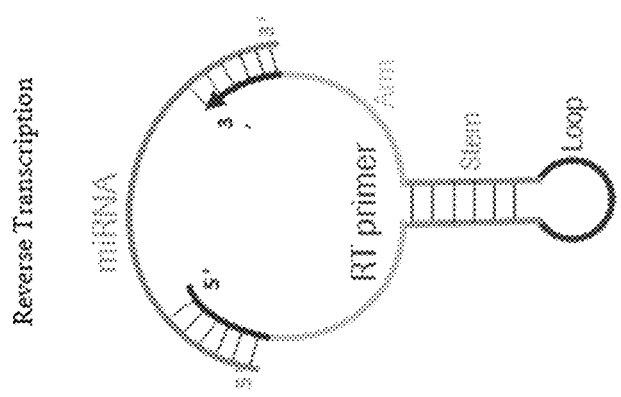
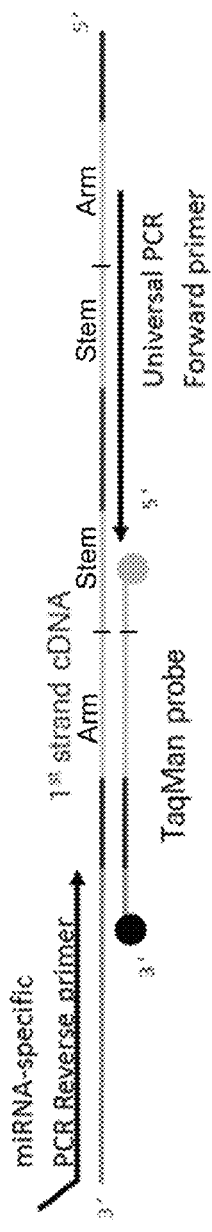
Figure 1A
Figure 1B

MULTIPLEX DETECTION OF SHORT NUCLEIC ACIDS

CROSS REFERENCE TO RELATED APPLICATIONS

The present application claims priority to U.S. Application No. 62/558,209, filed Sep. 13, 2017, the disclosure of which is incorporated by reference herein in its entirety.

SEQUENCE LISTING

The instant application contains a Sequence Listing which has been submitted electronically in ASCII format and is hereby incorporated by reference in its entirety. Said ASCII copy, created on Jul. 23, 2018, is named 34454-US1_SL.txt and is 708 bytes in size.

BACKGROUND OF THE INVENTION

Non-invasive sample collection (e.g., blood, plasma, saliva, urine) is becoming more common, encouraged by ease and reduced cost of sample collection. Nucleic acid biomarkers in liquid biopsies are often short, e.g., less than 250 nucleotides in length. Examples of disease associated biomarkers in liquid biopsies are miRNA molecules, several of which have been found at abnormal levels in various disease states. miRNA molecules are typically 16-30 nucleotides in length.

Biomarker nucleic acids are typically quite rare in a liquid biopsy, so amplification of the biomarker nucleic acid is advantageous to increase sensitivity of detection. Specific amplification of short nucleic acid sequences, however, is challenging. Amplification primers are often in the range of 15-25 nucleotides, and shorter complementary sequences can result in reduced specificity. Thus, while amplification and detection techniques typically require two primers and a probe, each of these elements can be about the same size as the targeted nucleic acids in a liquid biopsy.

One approach to amplification and detection of short nucleic acid sequences is disclosed in WO2016027162. This document discloses RT-qPCR detection of miRNA and other short nucleic acids using a two-tailed reverse transcription (RT) primer. The previously disclosed two-tailed primer is designed for detection of one miRNA per RT and PCR well, and uses target-specific forward and reverse PCR primers.

For many diagnostic applications it is desirable to monitor levels of more than one biomarker, as well as external and/or internal controls for each sample. The present disclosure provides novel compositions and methods for specific multiplex amplification and detection of short nucleic acids.

SUMMARY OF THE INVENTION

Provided herein are primers, kits, assays, and methods for detecting short nucleic acids in multiplex.

In some embodiments, a reaction mixture is provided, said reaction mixture comprising:
a) a first two-tailed primer comprising from 5' to 3':
   i) a sequence complementary to the 5' end of a first target nucleic acid;
   ii) a first arm sequence;
   iii) a first stem sequence;
   iv) a loop sequence;
   v) a second stem sequence complementary to the first stem sequence;
   vi) a second arm sequence; and
   vii) a sequence complementary to the 3' end of the first target nucleic acid;
b) a second two-tailed primer comprising from 5' to 3':
   i) a sequence complementary to the 5' end of a second target nucleic acid;
   ii) the first arm sequence;
   iii) the first stem sequence;
   iv) the loop sequence;
   v) the second stem sequence complementary to the first stem sequence;
   vi) the second arm sequence; and
   vii) a sequence complementary to the 3' end of the second target nucleic acid;
c) a first target specific reverse PCR primer complementary to the reverse transcription product of the first target nucleic acid;
d) a second target specific reverse PCR primer complementary to the reverse transcription product of the second target nucleic acid;
e) a universal forward PCR primer complementary to the first arm sequence, first stem sequence and/or loop sequence;
f) a first detectably labeled probe comprising 5' to 3:
   i) a sequence complementary to the second stem sequence and/or the second arm sequence; and
   ii) a sequence complementary to the sequence complementary to the 3' end of the first target nucleic acid; and
   iii) a sequence complementary to the reverse transcription product of the first target nucleic acid; and
g) a second detectably labeled probe comprising 5' to 3:
   i) a sequence complementary to the second stem sequence and/or the second arm sequence; and
   ii) a sequence complementary to the sequence complementary to the 3' end of the second target nucleic acid; and
   iii) a sequence complementary to the reverse transcription product of the second target nucleic acid.

In some embodiments, the reaction mixture further comprises:
h) a third two-tailed primer comprising from 5' to 3':
   i) a sequence complementary to the 5' end of a third target nucleic acid;
   ii) the first arm sequence;
   iii) the first stem sequence;
   iv) the loop sequence;
   v) the second stem sequence complementary to the first stem sequence;
   vi) the second arm sequence; and
   vii) a sequence complementary to the 3' end of the third target nucleic acid;
i) a third target specific reverse PCR primer complementary to the reverse transcription product of the third target nucleic acid; and
j) a third detectably labeled probe comprising 5' to 3:
   i) a sequence complementary to the second stem sequence and/or the second arm sequence;
   ii) a sequence complementary to the sequence complementary to the 3' end of the third target nucleic acid; and
   iii) a sequence complementary to the reverse transcription product of the third target nucleic acid.

In some embodiments, the reaction mixture further comprises:
k) a fourth two-tailed primer comprising from 5' to 3':
   i) a sequence complementary to the 5' end of a fourth target nucleic acid;
   ii) the first arm sequence;
   iii) the first stem sequence;

iv) the loop sequence;
v) the second stem sequence complementary to the first stem sequence;
vi) the second arm sequence; and
vii) a sequence complementary to the 3' end of the fourth target nucleic acid;
l) a fourth target specific reverse PCR primer complementary to the reverse transcription product of the fourth target nucleic acid; and
m) a fourth detectably labeled probe comprising 5' to 3:
i) a sequence complementary to the second stem sequence and/or the second arm sequence; and
ii) a sequence complementary to the sequence complementary to the 3' end of the fourth target nucleic acid; and
iii) a sequence complementary to the reverse transcription product of the fourth target nucleic acid.

In some embodiments, the sequences complementary to the 5' ends of each of the target nucleic acids are independently 4-10 nucleotides in length (e.g., each independently 4, 5, 6, 7, 8, 9, or 10 nucleotides).

In some embodiments, the detectably labeled probes are labeled with a fluorophore (e.g., a different fluorophore for each target-specific probe). In some embodiments, the detectably labeled probe is labeled with a fluorophore and a quencher. In some embodiments, at least one detectably labeled probe includes a modified nucleotide, e.g., an LNA nucleotide.

In some embodiments, at least one target nucleic acid is an RNA molecule between 15 and 50 nucleotides in length (e.g., between 16-30, or 18-25 nucleotides). In some embodiments, all of the target nucleic acids are RNA molecules between 15 and 50 nucleotides in length (e.g., miRNA, or other fragmented cell free RNA).

Further provided are methods for specific multiplex detection of RNA molecules between 15 and 50 nucleotides in length comprising:
a) contacting a sample comprising at least one target nucleic acid with a reaction mixture as described herein,
b) carrying out a reverse transcription reaction with the mixture of step a) to form a reverse transcription product;
c) carrying out a PCR reaction with the reverse transcription product of step b) to form an amplification product of at least one target nucleic acid; and
d) detecting the amplification product, thereby specifically detecting at least one RNA molecule between 15 and 50 nucleotides in length.

BRIEF DESCRIPTION OF THE DRAWINGS

FIG. 1A and FIG. 1B show schematics of the reverse transcription and real time PCR steps, respectively. FIG. 1A shows the two-tailed RT-PCR primer hybridized to a short nucleic acid (miRNA). In a multiplex reaction, all RT primers have the same arm-stem-loop sequence, but differ in the 5' and 3' ends specific for the target sequence. The RT primers thus discriminate between multiple targets in the RT reaction. FIG. 1B shows the subsequent PCR reaction with the product of the RT reaction (1$^{st}$ strand cDNA) and exemplary positions of the primers and probe. The probe includes target specific sequence at the 3' end, and universal arm and stem sequence at the 5' end. The reverse primer is target specific (miRNA-specific PCR reverse primer) and the PCR forward primer is universal. The use of universal PCR forward primers reduces the complexity of the oligonucleotides in the multiplex reaction.

FIG. 2A shows that the reaction with a universal forward primer resulted in a more efficient amplification curve than that with target specific forward primers. The no RNA control with target specific forward primers showed a signal, albeit with a Ct of about 36. This background amplification signal negatively impacts assay sensitivity and dynamic range. FIG. 2A thus shows that use of universal forward primer in the PCR step results in less background. Similarly, FIG. 2B shows again that the reaction with a universal forward primer resulted in a more efficient amplification curve. In FIG. 2B, the no RNA control with target specific forward primers showed a significant signal, with a Ct of about 32. FIG. 2B thus also shows that the universal forward primer has superior performance with less background.

FIG. 3A shows the amplification curve for PCR using non-modified probe. The positive control shows a strong signal with a Ct of about 30, but there is significant background (signal from cross-reactive cDNA) with a Ct of about 33. FIG. 3B shows the amplification curve for PCR using a LNA-modified probe. Again, the positive control performs well with a Ct of about 30, but the background signal is largely eliminated. FIG. 3B thus shows that modification of the probe significantly reduces background signal. This is especially true when target sequences in the reaction are similar in the 3' region that hybridizes to the probe.

DETAILED DESCRIPTION OF THE INVENTION

I. Introduction

Figure 2A:
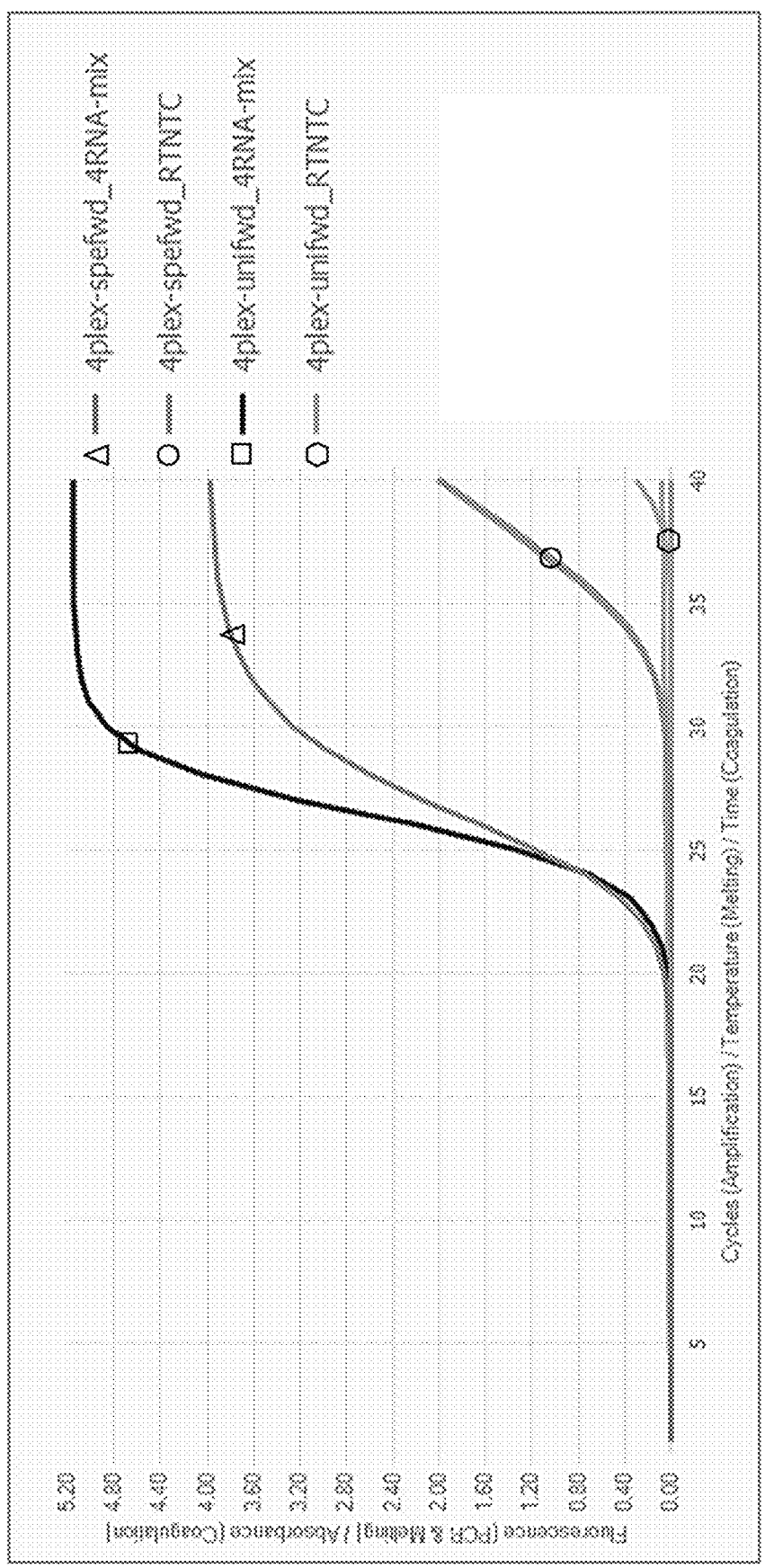
FIG. 2A and FIG. 2B compare amplification curves using universal PCR forward primers to those using target specific PCR forward primers. For both FIG. 2A and FIG. 2B, RTNTC=no RNA control; 4RNA-mix=mixture of 4 target RNAs (cDNA/DNA in PCR step); 4plex-spefwd=PCR using target specific forward primer; 4plex-unifwd=PCR using universal forward primer.

The present disclosure provides compositions and methods for specific multiplex amplification and detection of short nucleic acids such as miRNA. Provided are at least three elements that allow for specific and sensitive detection of short nucleic acids: (i) 2-tailed RT primers with the same arm, stem, and loop sequences to reduce complexity of the oligonucleotides involved in the RT reaction (see, e.g., FIG. 1A); (ii) a universal forward PCR primer to reduce the complexity of oligonucleotides involved in the PCR reaction and reduce non-specific amplification (see, e.g., FIG. 1B); and (iii) use of modified nucleic acids in probes that target similar target sequences to enhance probe specificity in a multiplex assay.

Regarding element (i), an approach to increase specificity of a multiplex reaction would be to use different arm, stem, and/or loop sequences on the two-tailed primer for each target in the multiplex reaction. However, this approach reduces the efficiency of the reaction, and multiplex target specificity can be addressed with probe design, e.g., using modified nucleotides.

II. Definitions

The terms "cell-free nucleic acids," "cell-free RNA," "cell-free DNA," and like terms in the context of the present disclosure refers to a non-tissue sample (e.g., liquid biopsy) from an individual that has been processed to largely remove cells. Examples of non-tissue samples include blood and blood components, urine, saliva, tears, mucus, etc.

The term "biomarker" can refer to any detectable marker used to differentiate individual samples, e.g., cancer versus non-cancer samples. Biomarkers include modifications (e.g., methylation of DNA, phosphorylation of protein), differential expression, and mutations or variants (e.g., single nucleotide variations, insertions, deletions, splice variants, and fusion variants). A biomarker can be detected in a DNA, RNA, and/or protein sample. In the case of an miRNA biomarker, the presence and amount of the targeted miRNA in a sample is typically determined.

The term "multiplex" refers to an assay in which more than one target is detected, e.g., in the same tube, well, or microchamber.

The terms "receptacle," "vessel," "tube," "well," "chamber," "microchamber," etc. refer to a containing space that can hold reagents or an assay. If the receptacle is in a kit and holds reagents, or is being used for an amplification reaction, it can be closed or sealed to avoid contamination or evaporation. If the receptacle is being used for an assay, it can be open or accessible, at least during set up of the assay.

The terms "individually detected" or "individual detection," referring to a marker gene or marker gene product, indicates that each marker in a multiplex reaction is detected. That is, each marker is associated with a different label (detected by a differently labeled probe).

The terms "nucleic acid," "polynucleotide," and "oligonucleotide" refer to polymers of nucleotides (e.g., ribonucleotides or deoxyribo-nucleotides) and includes naturally-occurring (e.g., adenosine, guanidine, cytosine, uracil and thymidine), and non-naturally occurring (human-modified) nucleic acids. The term is not limited by length (e.g., number of monomers) of the polymer. A nucleic acid may be single-stranded or double-stranded and will generally contain 5'-3' phosphodiester bonds, although in some cases, nucleotide analogs may have other linkages. Monomers are typically referred to as nucleotides. The term "non-natural nucleotide" or "modified nucleotide" refers to a nucleotide that contains a modified nitrogenous base, sugar or phosphate group, or that incorporates a non-natural moiety in its structure. Examples of non-natural nucleotides include LNA, dideoxynucleotides, biotinylated, aminated, deaminated, alkylated, benzylated and fluorophor-labeled nucleotides.

"LNA" refers to Locked Nucleic Acid. LNA is a modified RNA nucleotide in which the ribose moiety is modified with an extra bridge connecting the 2' oxygen and 4' carbon. LNA nucleotides can be mixed with DNA or RNA residues in any position in an oligonucleotide and hybridize with DNA or RNA according to Watson-Crick base-pairing rules. The locked ribose conformation enhances hybridization properties (e.g., increases melting temperatures).

The term "primer" refers to a short nucleic acid (an oligonucleotide) that acts as a point of initiation of polynucleotide strand synthesis by a nucleic acid polymerase under suitable conditions. Polynucleotide synthesis and amplification reactions typically include an appropriate buffer, dNTPs and/or rNTPs, and one or more optional cofactors, and are carried out at a suitable temperature. A primer typically includes at least one target-hybridized region that is at least substantially complementary to the target sequence (e.g., having 0, 1, or 2 mismatches). For the purposes of the present disclosure, this region of is typically about 4 to about 10 nucleotides in length, e.g., 5-8 nucleotides. A "primer pair" refers to a forward and reverse primer that are oriented in opposite directions relative to the target sequence, and that produce an amplification product in amplification conditions. The terms "forward" and "reverse" are assigned arbitrarily. One of ordinary skill in the art will understand that forward and reverse primers (primer pair) define the borders of an amplification product. In some embodiments, multiple primer pairs rely on a single common forward or reverse primer. For example, multiple allele-specific forward primers can be considered part of a primer pair with the same, common reverse primer, e.g., if the multiple alleles are in close proximity to each other.

As used herein, "probe" means any molecule that is capable of selectively binding to a specifically intended target biomolecule, for example, a nucleic acid sequence of interest that hybridizes to the probes. The probe is detectably labeled with at least one non-nucleotide moiety. In some embodiments, the probe is labeled with a fluorophore and quencher.

The words "complementary" or "complementarity" refer to the ability of a nucleic acid in a polynucleotide to form a base pair with another nucleic acid in a second polynucleotide. For example, the sequence A-G-T (A-G-U for RNA) is complementary to the sequence T-C-A (U-C-A for RNA). Complementarity may be partial, in which only some of the nucleic acids match according to base pairing, or complete, where all the nucleic acids match according to base pairing. A probe or primer is considered "specific for" a target sequence if it is at least partially complementary to the target sequence. Depending on the conditions, the degree of complementarity to the target sequence is typically higher for a shorter nucleic acid such as a primer (e.g., greater than 80%, 90%, 95%, or 98%) than for a longer sequence. In some embodiments, primers and/or probes are 100% complementary to the targeted sequence.

The term "specifically amplifies" indicates that a primer set amplifies a target sequence more than non-target sequence at a statistically significant level. The term "specifically detects" indicates that a probe will detect a target sequence more than non-target sequence at a statistically significant level. As will be understood in the art, specific amplification and detection can be determined using a negative control, e.g., a sample that includes the same nucleic acids as the test sample, but not the target sequence or a sample lacking nucleic acids. For example, primers and probes that specifically amplify and detect a target sequence result in a Ct that is readily distinguishable from background (non-target sequence), e.g., a Ct that is at least 2, 3, 4, 5, 5-10, 10-20, or 10-30 cycles less than background. The term "allele-specific" PCR refers to amplification of a target sequence using primers that specifically amplify a particular allelic variant of the target sequence. Typically, the forward or reverse primer includes the exact complement of the allelic variant at that position.

The terms "identical" or "percent identity," in the context of two or more nucleic acids, or two or more polypeptides, refer to two or more sequences or subsequences that are the same or have a specified percentage of nucleotides, or amino acids, that are the same (e.g., about 60% identity, e.g., at least any of 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters, or by manual alignment and visual inspection. See e.g., the NCBI web site at ncbi.nlm.nih.gov/BLAST. Such sequences are then said to be "substantially identical." Percent identity is typically determined over optimally aligned sequences, so that the definition applies to sequences that have deletions and/or additions, as well as those that have substitutions. The algorithms commonly used in the art account for gaps and the like. Typically, identity exists over a region comprising an a sequence that is at least about 8-25 amino acids or nucleotides in length, or over a region that is 50-100 amino acids or nucleotides in length, or over the entire length of the reference sequence.

The terms "isolate," "separate," "purify," and like terms are not intended to be absolute. For example, isolation of RNA does not require 100% of non-RNA molecules to be removed. One of skill in the art will recognize an acceptable level of purity for a given situation.

The term "kit" refers to any manufacture (e.g., a package or a container) including at least one reagent, such as a nucleic acid probe or probe pool or the like, for specifically amplifying, capturing, tagging/converting or detecting RNA or DNA as described herein.

The term "amplification conditions" refers to conditions in a nucleic acid amplification reaction (e.g., PCR amplification) that allow for hybridization and template-dependent extension of the primers. The term "amplicon" or "amplification product" refers to a nucleic acid molecule that contains all or a fragment of the target nucleic acid sequence and that is formed as the product of in vitro amplification by any suitable amplification method. The term "generate an amplification product" when applied to primers, indicates that the primers, under appropriate conditions (e.g., in the presence of a nucleotide polymerase and NTPs), will produce the defined amplification product. Various PCR conditions are described in *PCR Strategies* (Innis et al., 1995, Academic Press, San Diego, Calif.) at Chapter 14; *PCR Protocols: A Guide to Methods and Applications* (Innis et al., Academic Press, NY, 1990)

The term "amplification product" refers to the product of an amplification reaction. The amplification product includes the primers used to initiate each round of polynucleotide synthesis. An "amplicon" is the sequence targeted for amplification, and the term can also be used to refer to amplification product. The 5' and 3' borders of the amplicon are defined by the forward and reverse primers. A "reverse transcription product," "RT product," and like terms refers to a cDNA molecule produced by elongation of an RT primer on an RNA template by a polymerase with reverse transcriptase activity.

The terms "individual", "subject", and "patient" are used interchangeably herein. The individual can be pre-diagnosis, post-diagnosis but pre-therapy, undergoing therapy, or post-therapy. In the context of the present disclosure, the individual is typically seeking medical care.

The term "sample" or "biological sample" refers to any composition containing or presumed to contain nucleic acid. The term includes purified or separated components of cells, tissues, or blood, e.g., DNA, RNA, proteins, cell-free portions, or cell lysates. The sample can be FFPET, e.g., from a tumor or metastatic lesion. The sample can also be from frozen or fresh tissue, or from a liquid sample, e.g., blood or a blood component (plasma or serum), urine, semen, saliva, sputum, mucus, semen, tear, lymph, cerebral spinal fluid, mouth/throat rinse, bronchial alveolar lavage, material washed from a swab, etc. Samples also may include constituents and components of in vitro cultures of cells obtained from an individual, including cell lines. The sample can also be partially processed from a sample directly obtained from an individual, e.g., cell lysate or blood depleted of red blood cells.

The term "obtaining a sample from an individual" means that a biological sample from the individual is provided for testing. The obtaining can be directly from the individual, or from a third party that directly obtained the sample from the individual.

The term "providing therapy for an individual" means that the therapy is prescribed, recommended, or made available to the individual. The therapy may be actually administered to the individual by a third party (e.g., an in-patient injection), or by the individual herself.

A "control" sample or value refers to a value that serves as a reference, usually a known reference, for comparison to a test sample or test conditions. For example, a test sample can be taken from a test condition, e.g., from an individual suspected of having cancer, and compared to samples from known conditions, e.g., from a cancer-free individual (negative control), or from an individual known to have cancer or a target sequence of interest (positive control). In the context of the present disclosure, the test sample is typically from a cancer patient, or a patient suspected of having cancer. A control can also represent an average value or a range gathered from a number of tests or results. A control can also be prepared for reaction conditions. For example, a control for the presence, quality, and/or quantity of nucleic acid (e.g., internal control) can include primers or probes that will detect a sequence known to be present in the sample (e.g., a housekeeping gene such as beta actin, beta globin, glyceraldehyde 3-phosphate dehydrogenase (GAPDH), ribosomal protein L37 and L38, PPIase, EIF3, eukaryotic translation elongation factor 2 (eEF2), DHFR, or succinate dehydrogenase). In some embodiments, the internal control can be a sequence from a region of the same gene that is not commonly variant (e.g., in a different exon). A known added polynucleotide, e.g., having a designated length, can also be added. An example of a negative control is one free of nucleic acids, or one including primers or probes specific for a sequence that would not be present in the sample, e.g., from a different species. One of skill will understand that the selection of controls will depend on the particular assay, e.g., so that the control is cell type and organism-appropriate. One of skill in the art will recognize that controls can be designed for assessment of any number of parameters. For example, a control can be devised to compare therapeutic benefit based on pharmacological data (e.g., half-life) or therapeutic measures (e.g., comparison of benefit and/or side effects). Controls can be designed for in vitro applications. One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

The terms "label," "tag," "detectable moiety," and like terms refer to a composition detectable by spectroscopic, photochemical, biochemical, immunochemical, chemical, or other physical means. For example, useful labels include fluorescent dyes (fluorophores), luminescent agents, radio-isotopes (e.g., $^{32}P$, $^{3}H$), electron-dense reagents, or an affinity-based moiety, e.g., a poly-A (interacts with poly-T) or poly-T tag (interacts with poly-A), a His tag (interacts with Ni), or a strepavidin tag (separable with biotin). One of skill will understand that a detectable label conjugated to a nucleic acid is not naturally occurring.

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007); Sambrook et al., MOLECULAR CLONING, A LABORATORY MANUAL, Cold Springs Harbor Press (Cold Springs Harbor, N.Y. 1989). The term "a" or "an" is intended to mean "one or more." The terms "comprise," "comprises," and "comprising," when preceding the recitation of a step or an element, are intended to mean that the addition of further steps or elements is optional and not excluded.

III. Nucleic Acid Samples

Samples for biomarker detection can be obtained from any source suspected of containing nucleic add, e.g., tissue, skin, swab (e.g., buccal, vaginal), urine, saliva, etc. In some embodiments of the present disclosure, the sample is obtained from blood or a blood fraction.

In a sample that includes cells, the cells can be separated out (e.g., using size-based filtration or centrifugation), thereby leaving cell free nucleic acids (cfNA), including nucleic acids in exosomes, microvesicles, viral particles, or those circulating freely.

Methods for isolating nucleic acids from biological samples are known, e.g., as described in Sambrook, and several kits are commercially available (e.g., High Pure RNA Isolation Kit, High Pure Viral Nucleic Acid Kit, and MagNA Pure LC Total Nucleic Acid Isolation Kit, DNA Isolation Kit for Cells and Tissues, DNA Isolation Kit for Mammalian Blood, High Pure FFPET DNA Isolation Kit, available from Roche). In the context of the presently disclosed methods, RNA is collected, though in some embodiments, DNA can be collected and isolated.

IV. Cancer Associated Nucleic Acids

The presently disclosed methods are useful for detecting biomarkers present in a blood sample from an individual suffering from or at risk of disease. In particular, blood components are known to carry disease-associated biomarkers, e.g., in nucleic acids carried in the blood. Cell-free nucleic acids, e.g., in serum and plasma, are typically present in 50-200 nucleotide fragments, though miRNA molecules from liquid biopsies can be in the range of 15-50 or 16-30 nucleotides in length.

A comprehensive source for cancer mutations associated with cancer is the COSMIC (Catalog of Somatic Mutations in Cancer) database, available at the website cancer.sanger.ac.uk (Version 81 May 2017). The COSMIC database categorizes biomarkers in a number of ways, including tissue of origin, therapeutic effect, and signaling pathway. Thus, a medical provider can select markers associated, e.g., prostate cancer for a patient with prostate cancer, and later interrogate the database for mutations associated with drug resistance if the patient does not respond or relapses in response to first line therapy.

Resources from NCBI provide information on other disease-related biomarkers. These include Online Mendelian Inheritance in Man (OMIM) and the database of Genomes and Phenotypes (dbGaP). Thus, similar to COSMIC, a medical provider can query the databases for a given disease, e.g., diabetes, and find relevant biomarkers.

Detection of a disease associated biomarker can be used to diagnose disease, predict the likelihood of developing disease, select an appropriate treatment for a patient, monitor therapeutic progress of a patient undergoing therapy, or provide a prognosis for a patient.

In some embodiments, targeted therapy is prescribed, provided, or administered to the patient based on the presence or absence of a disease associated biomarker. Several drugs are designed specifically for patients with certain biomarker profiles (e.g., Tarceva and Tagrisso for certain EGFR mutations). New targeted therapies are being developed to address a number of specific mutations, thus one of skill in the art will be in the best position to select a targeted therapy for an individual at the time.

In addition, cancer patients can benefit from standard chemotherapy. Thus, in some embodiments, chemotherapy is prescribed, provided, or administered to the patient based on the presence or absence of a cancer-associated biomarker. This can include CHOP (cyclophosphamide; doxorubicin; vincristine; and prednisolone) or R-CHOP, which further includes rituximab and/or etoposide. The cocktail can be administered periodically for a set period of time, or until reduction in tumor size and/or symptoms are detected. For example, the CHOP or R-CHOP can be administered every 2 or 3 weeks.

Regardless of which treatment is selected, it typically begins with a low dose so that side effects can be determined, and the dose increased, e.g., until side effects appear or within the patient's tolerance, or until clinical benefit is observed.

V. Amplification and Detection

A nucleic acid sample can be used for detection and quantification, e.g., using nucleic acid amplification, e.g., using multiplex amplification using a two-tailed RT-PCR primer. For detection of a biomarker in an RNA sample, a preliminary reverse transcription step is carried out (also referred to as RT-PCR, not to be confused with real time PCR). See, e.g., Hierro et al. (2006) 72:7148. The term "qRT-PCR" as used herein refers to reverse transcription and quantitative PCR. Both reactions can be carried out in a single tube without interruption, e.g., to add reagents. For example, a polyT primer can be used to reverse transcribe all mRNAs in a sample with a polyA tail, random oligonucleotides can be used, or a primer can be designed that is specific for a particular target transcript that will be reverse transcribed into cDNA. The cDNA, or DNA from the sample, can form the initial template to be for quantitative amplification (real time or quantitative PCR, i.e., RTPCR or qPCR). qPCR allows for reliable detection and measurement of products generated during each cycle of PCR process. Such techniques are well known in the art, and kits and reagents are commercially available, e.g., from Roche Molecular Systems, Life Technologies, Bio-Rad, etc. See, e.g., Pfaffl (2010) *Methods: The ongoing evolution of qPCR* vol. 50.

A separate reverse transcriptase and thermostable DNA polymerase can be used, e.g., in a two-step (reverse transcription followed by addition of DNA polymerase and amplification) or combined reaction (with both enzymes added at once). In some embodiments, the target nucleic acid is amplified with a thermostable polymerase with both reverse transcriptase activity and DNA template-dependent activity. Exemplary enzymes include Tth DNA polymerase, the C. therm Polymerase system, and those disclosed in US20140170730 and US20140051126.

Probes for use as described herein can be labeled with a fluorophore and optionally a quencher (e.g., TaqMan, Light-Cycler, Molecular Beacon, Scorpion, or Dual Labeled probes). Appropriate fluorophores include but are not limited to FAM, JOE, TET, Cal Fluor Gold 540, HEX, VIC, Cal Fluor Orang 560, TAMRA, Cyanine 3, Quasar 570, Cal Fluor Red 590, Rox, Texas Red, Cyanine 5, Quasar 670, and Cyanine 5.5. Appropriate quenchers include but are not limited to TAMRA (for FAM, JOE, and TET), DABCYL, and BHQ1-3.

Detection devices are known in the art and can be selected as appropriate for the selected labels. Detection devices appropriate for quantitative PCR include the Cobas® and Light Cycler® systems (Roche), PRISM 7000 and 7300 real-time PCR systems (Applied Biosystems), etc. Six-channel detection is available on the CFX96 Real Time PCR Detection System (Bio-Rad) and Rotorgene Q (Qiagen), allowing for a higher degree of multiplexing.

For PCR detection, results can be expressed in terms of a threshold cycle (abbreviated as Ct, and in some instances Cq or Cp). A lower Ct value reflects the rapid achievement of a predetermined threshold level, e.g., because of higher target nucleic acid concentration or a more efficient amplification. A higher Ct value may reflect lower target nucleic acid concentration, or inefficient or inhibited amplification. The threshold cycle is generally selected to be in the linear range of amplification for a given target. In some embodiments, the Ct is set as the cycle at which the growth signal exceeds a pre-defined threshold line, e.g., in relation to the baseline, or by determining the maximum of the second derivation of the growth curve. Determination of Ct is known in the art, and described, e.g., in U.S. Pat. No. 7,363,168.

In some embodiments, digital PCR (dPCR) can be used to detect a cancer associated biomarker. For example, digital droplet PCR (ddPCR) can be used to determine absolute measurement of a target nucleic acid in a sample, even at very low concentrations. The dPCR method comprises the steps of digital dilution or droplet generation, PCR amplification, detection and (optionally) analysis. The partitioning step comprises generation of a plurality of individual reaction volumes (e.g., droplets or partitions) each containing reagents necessary to perform nucleic acid amplification. The PCR amplification step comprises subjecting the partitioned volumes to thermocycling conditions suitable for amplification of the nucleic acid targets to generate amplicons. Detection comprises identification of those partitioned volumes that contain and do not contain amplicons. The analysis step comprises a quantitation that yields e.g., concentration, absolute amount or relative amount (as compared to another target) of the target nucleic acid in the sample. Commercially available dPCR systems are available, e.g., from Bio-Rad and ThermoFisher. Descriptions of dPCR can be found, e.g., in US20140242582; Kuypers et al. (2017) *J Clin Microbiol* 55:1621; and Whale et at (2016) *Biomol Detect Quantif* 10:15.

In some embodiments, the disease-associated biomarker is detected using sequencing, e.g., massively parallel sequencing (MPS) or next-generation sequencing (NGS). Next-generation sequencing methods clonally propagate millions of single DNA molecules in parallel. Each clonal population is then individually sequenced. NGS methods include sequencing by synthesis (e.g., Illumina), nanopore sequencing (e.g., Oxford Nanopore Technologies), single molecule real-time sequencing (e.g., Pacific Biosciences), ion semiconductor based sequencing (Ion Torrent), and pyrosequencing (454/Roche). Cell-free nucleic acids are present in short fragments, e.g., about 50-200 bp, thus read length limitations of the sequencing method is unlikely to be an issue. In some embodiments, the sequencing method comprises an optional target enrichment step, e.g., an amplification step. In other embodiments, other target enrichment methods are used, e.g., library-based or probe-based methods of target enrichment (e.g., U.S. Pat. No. 7,867,703 or 8,383,338). NGS methods are described, e.g., in Xu, *Next Generation Sequencing: Current Technologies and Application*, Caister Acad. Press 2014; Ma et al. (2017) *Biomicrofluidics* 11:021501; Kelly (2017) *Semin Oncol Nurs* 33:208; and Serrati et al. (2016) *Onco Targets Ther* 9:7355.

VI. Kits

Provided herein are kits for carrying out multiplex amplification using a two-tailed RT-PCR primer.

In some embodiments, the kit comprises a blood collection vessel (e.g., tube, vial, multi-well plate or multi-vessel cartridge).

In some embodiments, the kit includes reagents and/or components for nucleic acid purification. For example, the kit can include a lysis buffer (e.g., comprising detergent, chaotropic agents, buffering agents, etc.), enzymes or reagents for denaturing proteins or other undesired materials in the sample (e.g., proteinase K, DNase), enzymes to preserve nucleic acids (e.g., DNase and/or RNase inhibitors). In some embodiments, the kit includes components for nucleic acid separation, e.g., solid or semi-solid matrices such as chromatography matrix, magnetic beads, magnetic glass beads, glass fibers, silica filters, etc. In some embodiments, the kit includes wash and/or elution buffers for purification and release of nucleic acids from the solid or semi-solid matrix. For example, the kit can include components from MagNA Pure LC Total Nucleic Acid Isolation Kit, DNA Isolation Kit for Mammalian Blood, High Pure or MagNA Pure RNA Isolation Kits (Roche), DNeasy or RNeasy Kits (Qiagen), PureLink DNA or RNA Isolation Kits (Thermo Fisher), etc.

In some embodiments, the kit includes reagents for detection of particular target nucleic acids, e.g., target nucleic acids associated with cancer or other disease. For example, the kit can include oligonucleotides that specifically bind to cancer-associated biomarkers such as certain miRNAs, mutations, or sequences known to have copy number variations in cancer. In some embodiments, the detection reagents are for RT-PCR, qRT-PCR, qPCR, dPCR, sequencing (Sanger or NGS).

The kit can further include reagents for amplification, e.g., reverse transcriptase, DNA polymerase, dNTPs, buffers, and/or other elements (e.g., cofactors or aptamers) appropriate for reverse transcription and/or amplification. Typically, the reagent mixture(s) is concentrated, so that an aliquot is added to the final reaction volume, along with sample (e.g., RNA or DNA), enzymes, and/or water. In some embodiments, the kit further comprises reverse transcriptase (or an enzyme with reverse transcriptase activity), and/or DNA polymerase (e.g., thermostable DNA polymerase such as Taq, ZO5, and derivatives thereof).

In some embodiments, the kit further includes at least one control sample, e.g., nucleic acids from non-disease sample (or pooled samples), or from a sample known to carry a target sequence (or pooled samples). In some embodiments, the kit includes a negative control, e.g., lacking nucleic acids, or lacking the targeted nucleic acid sequence. In some embodiments, the kit further includes consumables, e.g., plates or tubes for nucleic acid preparation, tubes for sample collection, or plates, tubes, or microchips for PCR or qRT-PCR. In some embodiments, the kit further includes instructions for use, reference to a website, or software.

VII. Examples

Figure 2B:
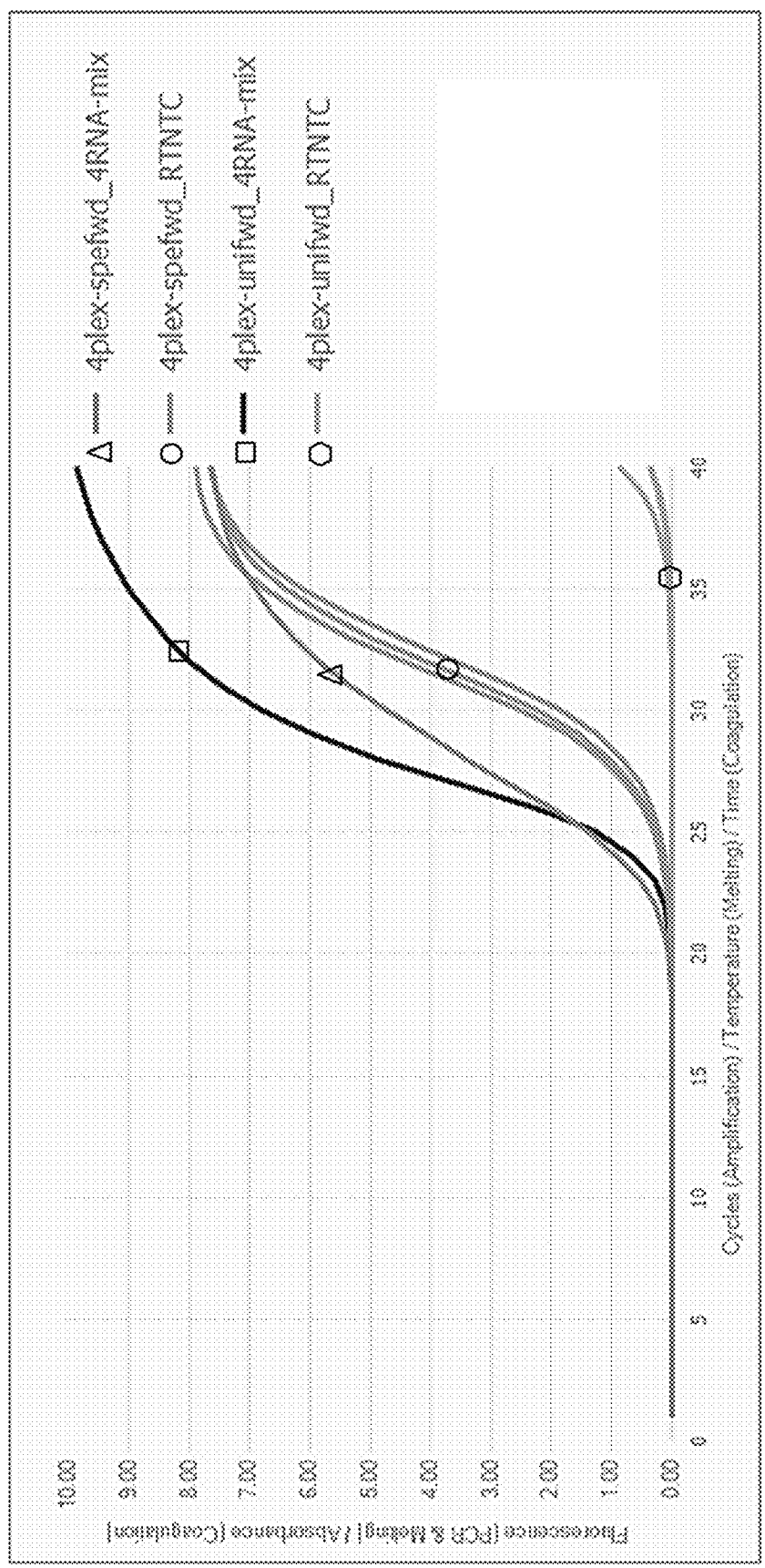

Example 1: Use of Universal Primer in Multiplex Assay Improves Specificity and Signal Strength The presently disclosed results show that use of a single forward primer that is complementary to a portion of all reverse transcription products (e.g., spanning arm, step, and/or loop sequences from the RT primer) results in little or no non-specific amplification. See FIG. 1A and FIG. 1B for schematics of the primers. FIG. 2A and FIG. 2B compares results from RT-qPCR run with target specific forward primers (4plex-spefwd) and universal forward primers (4plex-unifwd). The no RNA negative controls in FIG. 2A and FIG. 2B show significantly higher signals with the target specific forward primers compared to the universal primer. Moreover, the signals for RNA positive samples are not as strong in reactions with the target specific forward primers compared to those using the universal primer. The four target RNA molecules were miR-39 (external control), miR-21 (lung cancer biomarker), miR-423 (internal control), and miR-126 (lung cancer biomarker).

Example 2: Probe Modification Reduces Cross-Reactivity in Multiplex Assay

When target RNA molecules have similar sequences at the 3' end, probes can cross-react. One option for addressing specificity in a multiplex reaction is to have RT primers for a set of miRNAs combined in the RT reaction. Then, an aliquot of the cDNA is amplified using a mix of forward and reverse PCR primers for the same set of miRNA targets (RT products) along with miRNA target specific probes in one PCR reaction. The probes in this case target the sequence between the forward and reverse primer of the $2^{nd}$ strand cDNA, and are labeled with a distinct fluorophore for each miRNA target for specific detection. In this design scheme, the probes share the same 5' end, targeting arm, stem, and/or loop sequence, followed by 8-10 target-specific nucleotides. This approach is problematic for some miRNAs with very similar 3' sequences because the probes would only differ by a few nucleotides near the 3' end and lead to cross reactivity or non-specific detection.

Another option to increase specificity of the probes is to design 2 tailed RT-primers with different arm, stem, and/or loop sequences that enable detection of various miRNA by arm/stem/loop-specific probes. We found that the different arm/stem/loop sequences provide high specificity of the probes for the detection of similar miRNAs. However the different arm/stem/loop sequences in the RT primers increases the complexity of the oligonucleotides in the RT reaction even further and lead to even stronger formation of primer dimers resulting in non-specific signal in the PCR reaction that prevents any meaningful measurements.

Figure 3A:
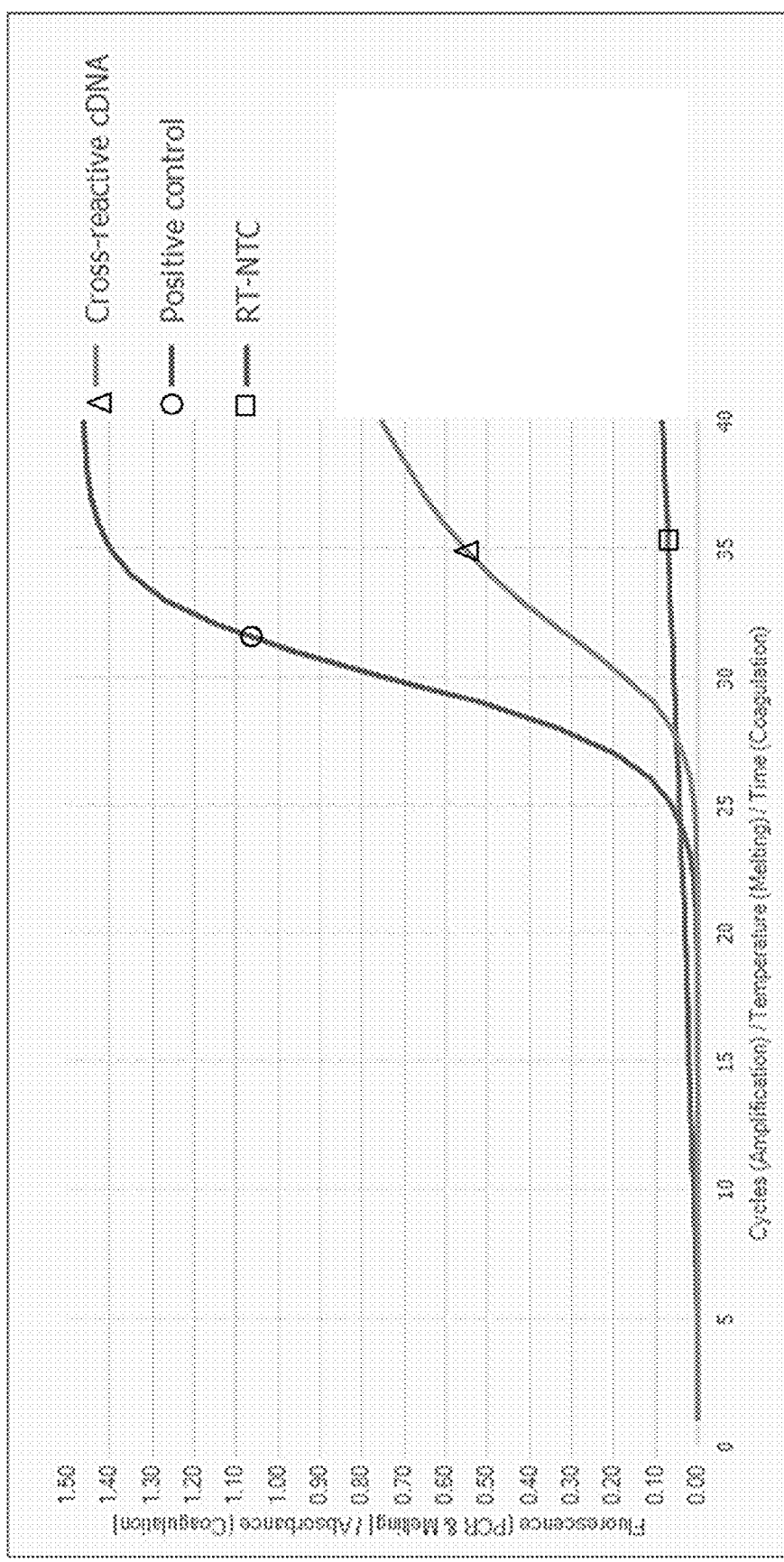
FIG. 3A and FIG. 3B show the effect of modification of the probe on signal and specificity.
Figure 3B:
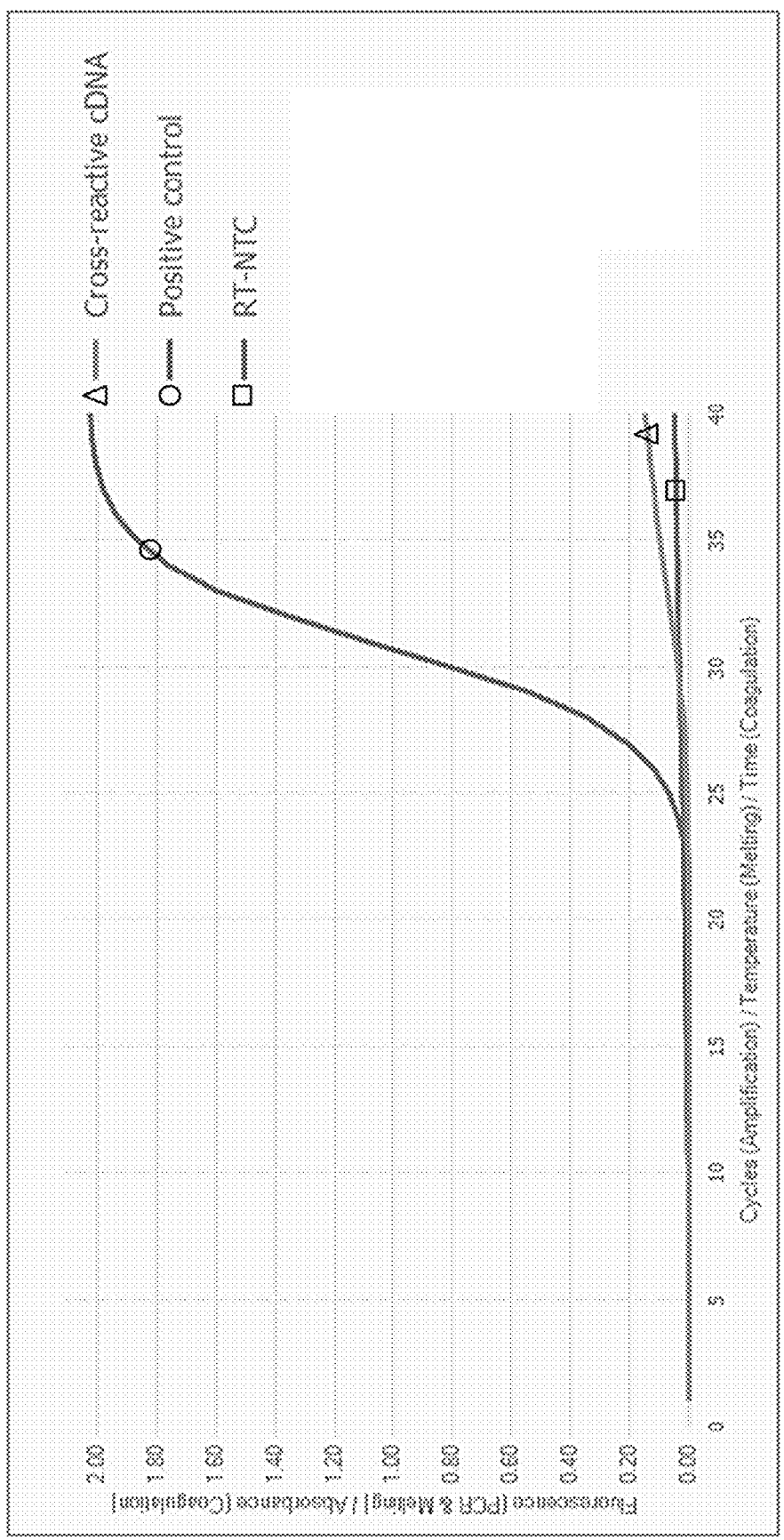

An example of targets with similar 3' end sequences are miR-126 and miR-16, and as explained above, routine multiplex designs generate probes that do not discriminate between the sequences well. FIG. 3A and FIG. 3B show results of RT-qPCR of these sequences using unmodified and modified probes, respectively. In this case, the probes were modified with LNA which increases hybridization specificity and Tm. FIG. 3A shows cross-reactivity in multiplex reaction using an unmodified miR-126 probe, with background appearing at about Ct 32. In contrast, FIG. 3B shows the result with an LNA modified miR-126 probe. Background signal is nearly undetectable.

The following probe sequences were used. The underlined nucleotides are those that hybridize to stem and/or arm sequence (from the RT primer) while the rest are miRNA target specific. Bolded nucleotides are LNA in modified nucleotide probes.

miR126:

(SEQ ID NO: 1)

5'FAM-<u>ACCATCTGCA</u>CGCATTATT-BHQ miR16:

(SEQ ID NO: 2)

5'FAM-<u>CATCTGCA</u>CACCAATA-BHQ

Example 3: Comparison to Existing Technologies

We compared results from the presently disclosed two-tailed RT primer approach to a 4 target multiplex reaction to those from single target assays for the same miRNA targets that are commercially available from ABI. The four miRNA targets are miR126, miR21, miR423, and miR39. The tables below show Ct values of titration RT-PCR reactions using the multiplex, two-tailed RT primer approach (top table) and the singleplex ABI assay (bottom table).

| RNA Mix | cDNA cps/rxn | Log 10 | miR126 | miR21 | miR423 | miR39 |
|---|---|---|---|---|---|---|
| E7 | 2E+06 | 6.30 | 19.88 | 19.95 | 20.73 | 21.54 |
| E6 | 2E+05 | 5.30 | 23.38 | 23.48 | 24.47 | 25.10 |
| E5 | 2E+04 | 4.30 | 27.18 | 27.32 | 28.21 | 28.81 |
| E4 | 2E+03 | 3.30 | 30.87 | 31.01 | 31.85 | 32.56 |
| E3 | 2E+02 | 2.30 | 34.36 | 34.64 | 35.69 | 36.27 |
| E2 | 2E+01 | 1.30 | 37.29 | 38.28 | 38.67 | 37.80 |
| | Min RTNTC | | 38.52 | 36.99 | 39.81 | 37.78 |
| | SLOPE | | −3.53 | −3.69 | −3.63 | −3.69 |
| | RSQ | | 0.9985 | 0.9999 | 0.9989 | 0.9999 |
| E7 | 2E+06 | 6.30 | 19.87 | 19.95 | 19.00 | 19.48 |
| E6 | 2E+05 | 5.30 | 23.58 | 23.61 | 22.19 | 23.30 |
| E5 | 2E+04 | 4.30 | 27.12 | 26.98 | 26.32 | 27.05 |
| E4 | 2E+03 | 3.30 | 30.97 | 30.39 | 29.55 | 30.80 |
| E3 | 2E+02 | 2.30 | 34.56 | 34.47 | 33.77 | 34.40 |
| E2 | 2E+01 | 1.30 | 38.38 | 37.36 | 38.33 | 37.66 |
| | Min RTNTC | | 38.08 | N/A | 37.50 | N/A |
| | SLOPE | | −3.68 | −3.52 | −3.69 | −3.66 |
| | RSQ | | 0.9999 | 0.9988 | 0.9978 | 0.9993 |

The results show that the sensitivity and specificity of the presently disclosed multiplex approach is similar to that of current singleplex assays. The amplification curves from the two approaches reveal more efficient amplification in the multiplex assays (data not shown). Thus, the presently disclosed multiplex assays are at least as good if not better than current singleplex methods.

While the invention has been described in detail with reference to specific examples, it will be apparent to one skilled in the art that various modifications can be made within the scope of this invention. Thus the scope of the invention should not be limited by the examples described herein. All patents, publications, websites, Genbank (or other database) entries disclosed herein are incorporated by reference in their entireties.

We claim:

1. A reaction mixture comprising:
a) a first two-tailed primer comprising from 5' to 3':
   i) a sequence complementary to the 5' end of a first target nucleic acid;
   ii) a first arm sequence;
   iii) a first stem sequence;
   iv) a loop sequence;
   v) a second stem sequence complementary to the first stem sequence;
   vi) a second arm sequence; and
   vii) a sequence complementary to the 3' end of the first target nucleic acid;
b) a second two-tailed primer comprising from 5' to 3':
   i) a sequence complementary to the 5' end of a second target nucleic acid;
   ii) the first arm sequence;
   iii) the first stem sequence;
   iv) the loop sequence;
   v) the second stem sequence complementary to the first stem sequence;
   vi) the second arm sequence; and
   vii) a sequence complementary to the 3' end of the second target nucleic acid;
c) a first target specific reverse PCR primer complementary to the reverse transcription product of the first target nucleic acid;
d) a second target specific reverse PCR primer complementary to the reverse transcription product of the second target nucleic acid;
e) a universal forward PCR primer homologous to the first arm sequence, first stem sequence and/or loop sequence, wherein the universal forward PCR primer does not comprise sequences homologous to the first or second target nucleic acid;
f) a first detectably labeled probe comprising 5' to 3':
   i) a sequence complementary to the second stem sequence and/or the second arm sequence; and
   ii) a sequence complementary to the sequence complementary to the 3' end of the first target nucleic acid; and
   iii) a sequence complementary to the reverse transcription product of the first target nucleic acid; and
g) a second detectably labeled probe comprising 5' to 3':
   i) a sequence complementary to the second stem sequence and/or the second arm sequence; and
   ii) a sequence complementary to the sequence complementary to the 3' end of the second target nucleic acid; and
   iii) a sequence complementary to the reverse transcription product of the second target nucleic acid.

2. The reaction mixture of claim 1, further comprising:
h) a third two-tailed primer comprising from 5' to 3':
   i) a sequence complementary to the 5' end of a third target nucleic acid;
   ii) the first arm sequence;
   iii) the first stem sequence;
   iv) the loop sequence;
   v) the second stem sequence complementary to the first stem sequence;
   vi) the second arm sequence; and
   vii) a sequence complementary to the 3' end of the third target nucleic acid;
i) a third target specific reverse PCR primer complementary to the reverse transcription product of the third target nucleic acid; and
j) a third detectably labeled probe comprising 5' to 3':
   i) a sequence complementary to the second stem sequence and/or the second arm sequence; and
   ii) a sequence complementary to the sequence complementary to the 3' end of the third target nucleic acid; and
   iii) a sequence complementary to the reverse transcription product of the third target nucleic acid.

3. The reaction mixture of claim 2, further comprising:
k) a fourth two-tailed primer comprising from 5' to 3':
   i) a sequence complementary to the 5' end of a fourth target nucleic acid;
   ii) the first arm sequence;
   iii) the first stem sequence;
   iv) the loop sequence;

v) the second stem sequence complementary to the first stem sequence;
vi) the second arm sequence; and
vii) a sequence complementary to the 3' end of the fourth target nucleic acid;
l) a fourth target specific reverse PCR primer complementary to the reverse transcription product of the fourth target nucleic acid; and
m) a fourth detectably labeled probe comprising 5' to 3':
i) a sequence complementary to the second stem sequence and/or the second arm sequence; and
ii) a sequence complementary to the sequence complementary to the 3' end of the fourth target nucleic acid; and
iii) a sequence complementary to the reverse transcription product of the fourth target nucleic acid.

4. The reaction mixture of any one of claim 1, 2, or 3, wherein the sequences complementary to the 5' ends of each of the target nucleic acids are independently 4-10 nucleotides in length.

5. The reaction mixture of claim 4, wherein the sequences complementary to the 5' ends of each of the target nucleic acids are independently 5-8 nucleotides in length.

6. The reaction mixture of claim 1, wherein the sequences complementary to the 3' ends of each of the target nucleic acids are independently 4-10 nucleotides in length.

7. The reaction mixture of claim 6, wherein the sequences complementary to the 3' ends of each of the target nucleic acids are independently 5-8 nucleotides in length.

8. The reaction mixture of claim 1, wherein the detectably labeled probes comprise a fluorophore and a quencher.

9. The reaction mixture of claim 1, wherein the detectably labeled probes are each labeled with a different label.

10. The reaction mixture of claim 1, wherein at least one of the detectably labeled probes includes at least one LNA nucleotide.

11. The reaction mixture of claim 1, further comprising a polymerase having reverse transcriptase activity and a DNA polymerase.

12. The reaction mixture of claim 1, further comprising a polymerase having reverse transcriptase activity and DNA polymerase activity.

13. The reaction mixture of claim 1, further comprising at least one target nucleic acid.

14. The reaction mixture of claim 13, wherein the at least one target nucleic acid is an RNA molecule between 15 and 50 nucleotides in length.

15. The reaction mixture of claim 14, wherein the RNA molecule is between 16 and 30 nucleotides in length.

16. A method for specific multiplex detection of RNA molecules between 15 and 50 nucleotides in length comprising:
a) contacting a sample comprising at least one target nucleic acid with the reaction mixture of claim 1;
b) carrying out a reverse transcription reaction with the mixture of step a) to form a reverse transcription product;
c) carrying out a PCR reaction with the reverse transcription product of step b) to form an amplification product of at least one target nucleic acid;
d) detecting the amplification product, thereby specifically detecting at least one RNA molecule between 15 and 50 nucleotides in length.

* * * * *

SEQUENCE LISTING

<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
accatctgca cgcattatt                                                       19

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
catctgcaca ccaata                                                          16